United States Patent
Kishi et al.

[11] Patent Number: 5,127,708
[45] Date of Patent: Jul. 7, 1992

[54] SEAT WITH FATIGUE LESSENING DEVICE

[75] Inventors: Yoichi Kishi, Yokosuka; Hideyuki Nagashima, Yokohama; Akira Mochizuki, Kanagawa; Takayuki Yanagishima, Yokosuka, all of Japan

[73] Assignee: Nissan Motor Co., Ltd., Yokohama, Japan

[21] Appl. No.: 551,360

[22] Filed: Jul. 12, 1990

[30] Foreign Application Priority Data

Jul. 14, 1989 [JP] Japan ................... 1-182066

[51] Int. Cl.⁵ .............................................. B60N 2/02
[52] U.S. Cl. .............................. 297/284 R; 297/284 E; 297/284 G; 297/DIG. 3
[58] Field of Search ............ 297/284, DIG. 3, 284 R, 297/284 C, 284 E, 284 B, 284 G

[56] References Cited

U.S. PATENT DOCUMENTS

| | | | |
|---|---|---|---|
| 4,634,179 | 1/1987 | Hashimoto et al. | 297/284 |
| 4,833,614 | 5/1989 | Saitoh et al. | 297/284 X |
| 4,840,425 | 6/1989 | Noble | 297/284 |

FOREIGN PATENT DOCUMENTS

| | | | |
|---|---|---|---|
| 291233 | 12/1986 | Japan | 297/284 |
| WO8900726 | 1/1989 | PCT Int'l Appl. | |

*Primary Examiner*—Peter R. Brown
*Attorney, Agent, or Firm*—Pennie & Edmonds

[57] ABSTRACT

A seat having a fatigue lessening device functions to repeatedly expand and contract a given part of a seat occupant holding portion of the seat. A fatigue sensor is employed which issues an information signal representative of the fatigue of the occupant. A computer controls the operation of the device at intervals which are derived from the information signal. The fatigue sensor counts the number of movement of the seat occupant and uses the counted number as the factor for representing the degree of the occupant's fatigue.

13 Claims, 6 Drawing Sheets

SEAT WITH FATIGUE LESSENING DEVICE

BACKGROUND OF THE INVENTION

1. Field of the Invention

The present invention relates in general to seats for motor vehicles and more particularly to seats of a shape-adjustable type which can change the shape of the seat to fit the occupant. More specifically, the present invention is concerned with shape-adjustable seats of a type in which the shape change of the seat is achieved by controlling air pressure in various air-bags installed in the seat.

2. Description of the Prior Art

Hitherto, various types of shape-adjustable seats have been proposed and put into practical use particularly in the field of motor vehicles.

One of them is disclosed in Japanese Patent First Provisional Publication No. 61-257333. The seat of this publication employs a plurality of air-bags which are installed in given portions of the seat. By changing the air-pressure in each air-bag, the shape of the seat is changed or adjusted. During a long time driving of the associated motor vehicle, a timer means operates to vary the air-pressure in the air-bags at regular intervals thereby to lessen the fatigue of the seat occupant.

However, in the above-mentioned conventional seat, the pressure changing operation for the air-bags during the long time driving is automatically carried out without respect to the degree of fatigue of the seat occupant. Thus, it often occurs that the pressure changing operation takes place even when the seat occupant is not so fatigued. This unnecessary operation causes the seat occupant to feel uncomfortable.

Figure 7:
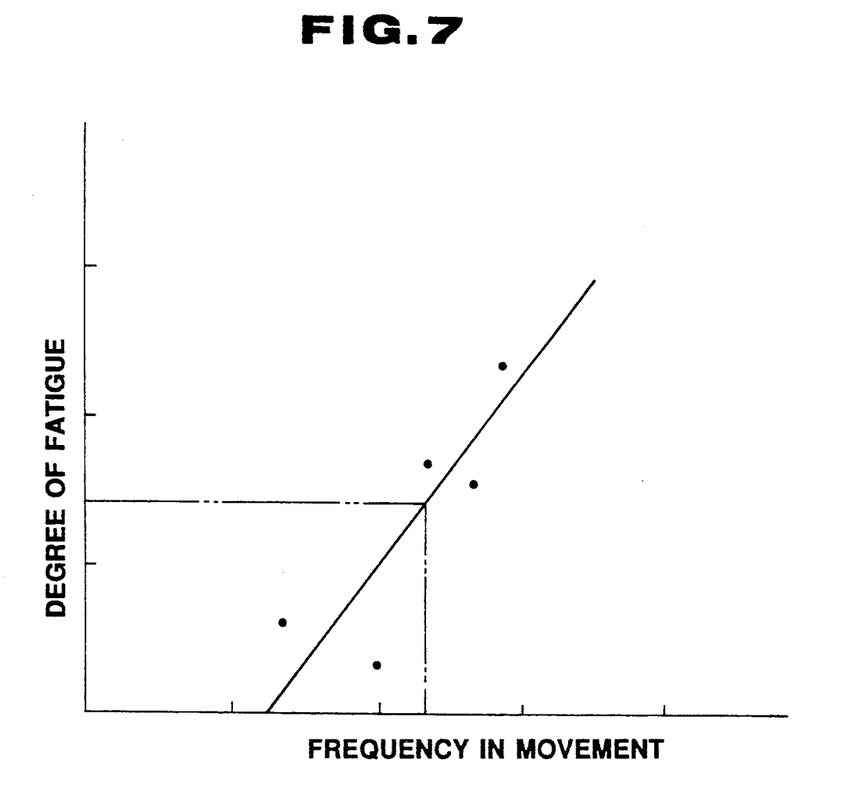
FIG. 7 is a graph showing a positive correlation between the frequency in movement of a seat occupant and the degree of fatigue of him or her.

The present inventors have found that, as is depicted by the graph of FIG. 7, the fatigue of a seat occupant has a close relationship to a frequency in movement of occupant. The graph shows that as the frequency in movement of the seat occupant increases, the degree of fatigue of him or her becomes high.

SUMMARY OF THE INVENTION

It is therefore an object of the present invention to provide a shape adjustable seat which is constructed by embodying the above-mentioned relationship found by the inventors.

According to the present invention, there is provided a shape adjustable seat which can change or vibrate a given portion or portions of the seat for a given time at intervals which are determined in accordance with the degree of fatigue of a seat occupant.

According to the present invention, there is provided a seat which comprises a shape changing means for changing the shape of a seat occupant holding portion of the seat; a fatigue detecting means for detecting the fatigue of a seat occupant; and a control means for controlling the shape changing means in accordance with the seat occupant's fatigue detected by the fatigue detecting means.

According to the present invention, there is provided a seat which comprises first means for changing the shape of a seat occupant holding portion of the seat; second means for controlling the first means at given intervals; third means for issuing an information signal representative of the degree of fatigue of a person who sits on the seat; and fourth means for determining the given intervals in accordance with said information signal given by the third means.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

Figure 1:
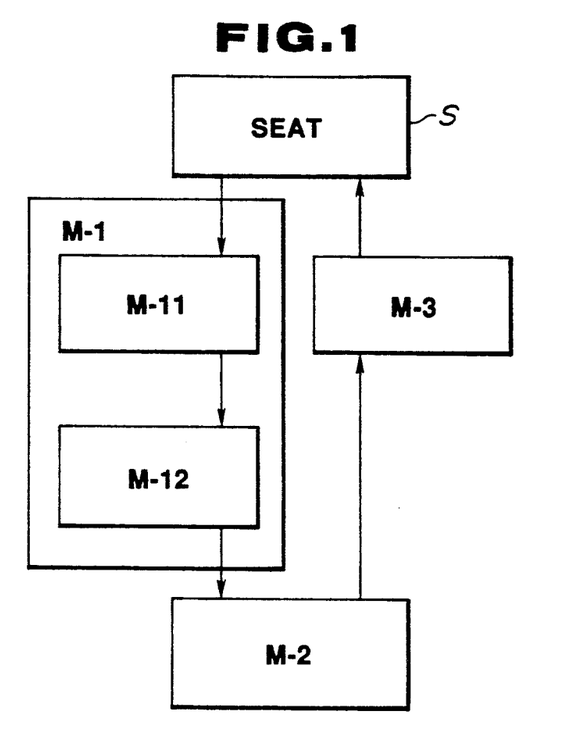
FIG. 1 is a block diagram depicting the concept of the present invention.

Referring to FIG. 1, there is shown a block diagram of the present invention, which generally comprises a fatigue sensing means "M-1", a control means "M-2" and a shaping means "M-3" which are incorporated with a seat proper "S" in a manner as will be described in the following. The fatigue sensing means "M-1" includes a seat occupant movement detecting means "M-11" and a movement frequency detecting means "M-12".

Figure 2:
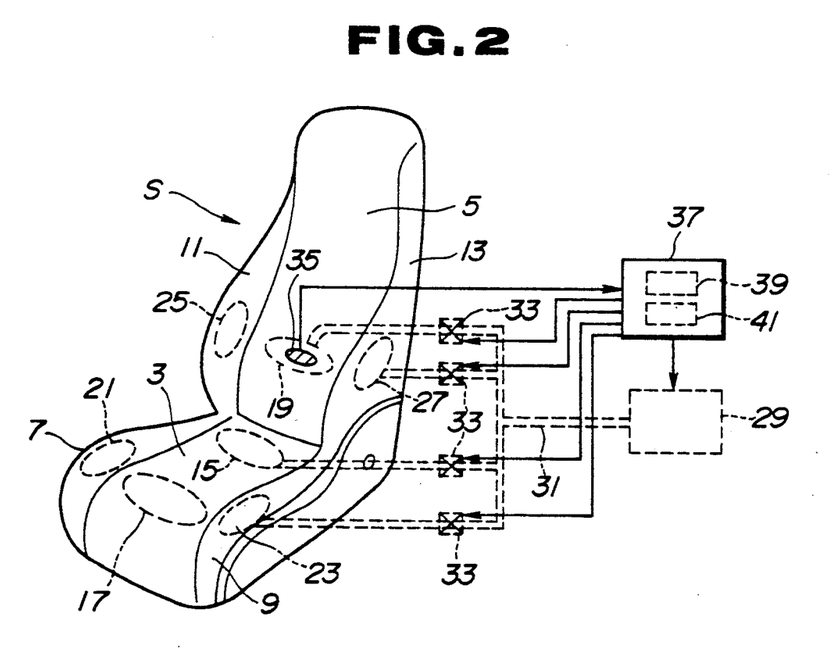
FIG. 2 is a perspective view of a shape adjustable seat which is a first embodiment of the present invention.

Referring to FIG. 2, there is shown an automotive seat S which is a first embodiment of the present invention.

The seat S comprises a seat cushion 3 and a seatback 5. The seat cushion 3 has side support portions 7 and 9 mounted to respective sides thereof, and the seatback 5 has also side support portions 11 and 13 mounted to respective sides thereof.

Within the seat cushion 3, there are installed a hip supporting air-bag 15 and a thigh supporting air-bag 17 which are arranged to support respectively the hip and thigh portions of a person who sits on the seat S.

Within the seatback 5, there is installed a lumbar supporting air-bag 19 which is arranged to support the lumbar portion of the seat occupant.

Within the side support portions 7 and 9 of the seat cushion 3, there are respectively installed side supporting air-bags 21 and 23 which are arranged to support side portions of the thighs of the seat occupant.

Within the side support portions 11 and 13 of the seatback 5, there are respectively installed side supporting air-bags 25 and 27 which are arranged to support sides of an upper half of the seat occupant.

All of the air-bags 15 to 27 are connected through branch pipes to an outlet pipe 31 of an electric air pump 29. It is to be noted that the air-bags 21 and 23 are communicated through a pipe (not shown) and the airbags 25 and 27 are communicated through another pipe (not shown). The branch pipes have electromagnetic valves 33 respectively connected thereto, which are controlled by a control unit including a microcomputer 37. The air-bags 15 to 27, the air-pump 29 and the valves 33 constitute the shaping means "M-3" for shaping the seat occupant holding portion of the seat S.

Thus, by controlling the valves 33 with an aid of the microcomputer 37, the amount of pressurized air fed to the air-bags 15 to 27 is changed or adjusted to provide the seat occupant holding portion of the seat S with a desired shape for the seat occupant.

Within the seat S, there is further installed a pressure sensor 35, such as a strain gauge or the like, which serves as the above-mentioned seat occupant movement detecting means "M-11". Information signals from this pressure sensor 35 are fed to the microcomputer 37 which serves as the above-mentioned control means "M-2".

In the disclosed embodiment, the pressure sensor 35 is installed in the seatback 5 at a position where the lumbar portion of a seat occupant is to be placed.

By analyzing the information signals from the pressure sensor 35, the computer 37 judges whether or not the movement of a seat occupant is caused by the fatigue of the occupant.

For this, the computer 37 has a memory by which a reference pressure value given when a seat occupant normally sits on the seat S is memorized. The data from the pressure sensor 35 is compared with the reference pressure value for carrying out the judgement. The computer 37 has also a counter 39 which serves as the above-mentioned movement frequency detecting means "M-12". When the pressure value detected by the pressure sensor 35 is found smaller than the reference value, the counter 39 counts "one" on the supposition that seat occupant has moved due to his increasing fatigue. When the number "N" counted by the counter 39 reaches to predetermined number "NR", the computer 37 controls the valve 33 of the lumbar supporting air bag 19 to repeatedly increase and decrease the pressure in the air-bag 19 on the judgement that the fatigue of the seat occupant has become marked. The computer 37 has also a timer 41.

Figure 3:
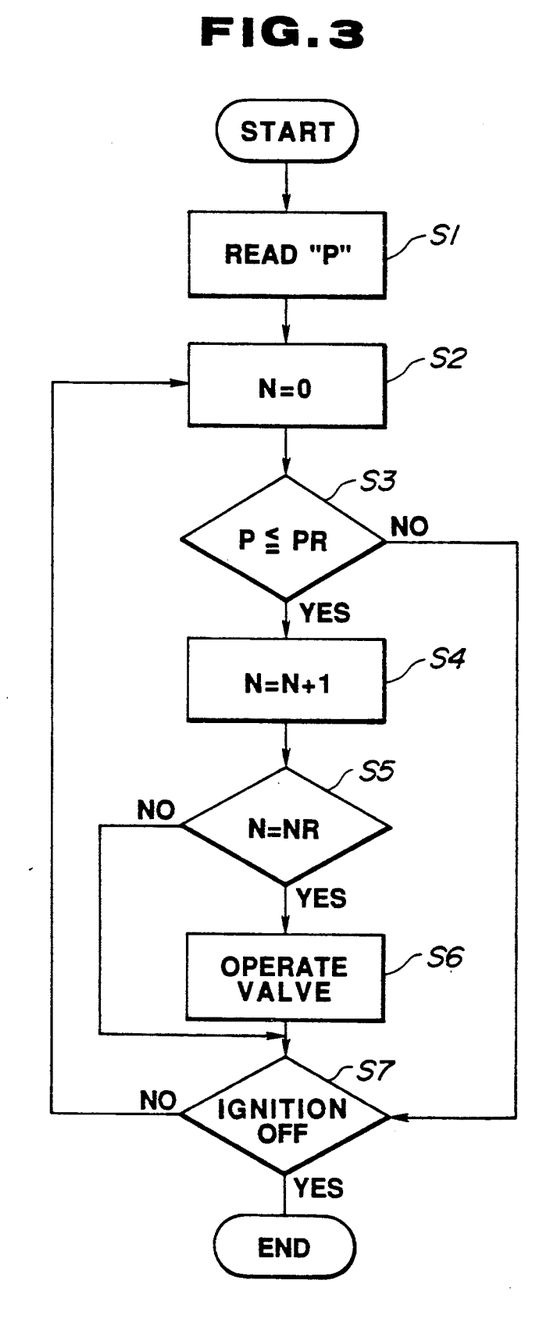
FIG. 3 is a flowchart which depicts the operation steps to be carried out by a micro-computer employed in the first embodiment.

The operation of the seat "S" of the first embodiment will be described in detail in the following with reference to the flowchart of FIG. 3.

Figure 6A:
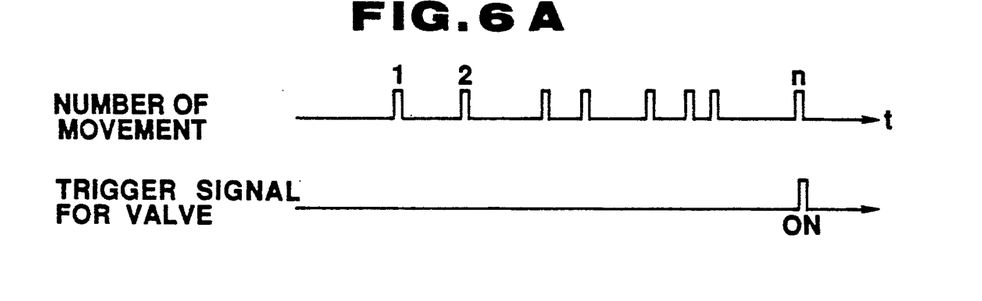
FIGS. 6A, 6B and 6C are pulse charts depicting the timing for operating an electromagnetic valve, which respectively correspond to the first, second and third embodiments.

When a person (for example, a driver) sitting on the seat "S" turns an ignition switch ON, the program starts and at step S1, a pressure "P" applied to the pressure sensor 35 by the seat occupant is read. Then, at step S2, the counter 39 is reset. Then, at step S3, a judgement is carried out as to whether or not the pressure "P" is smaller than the reference value "PR". If Yes, that is, when the pressure "P" is smaller than the reference value "PR", the counter counts "one" at step S4. (That is, when the seat occupant inclines his or her upper half part forward making the pressure "P" zero or lower than the reference value "PR", the computer 37 judges that he or she has moved due to his or her increasing fatigue.) If No, that is, when the pressure "P" is greater than the reference value "PR", the operation step goes to an after-mentioned step S7. At step S5, a judgement is carried out as to whether the number "N" counted by the counter 39 has reached to a predetermined number "NR" or not. (From the correlation depicted by the graph of FIG. 7, the reference number "NR" which represents the marked fatigue of the seat occupant is determined.) When Yes, that is, when the number "N" has reached the reference number "NR", a trigger signal is issued as is seen from FIG. 6A. Upon this, the computer 37 controls the valve 33 of the lumbar supporting air-bag 19 to repeat ON-OFF operation for a given time thereby to force the lumbar supporting air-bag 19 to repeat the expansion-contraction operation (step S6). Thus, the lumbar portion of the seat occupant is massaged lessening the fatigue of the occupant. If at step S5, it is judged that the number "N" has not reached the reference number "NR", the operation step goes to step S7. At step S7, a judgement is carried out as to whether the ignition switch is OFF or not. If No, that is, when the ignition switch is still ON, the operation step goes back to step S2 to repeat the above-mentioned steps. If Yes, that is, when the engine has been stopped, the control is stopped.

Figure 4:
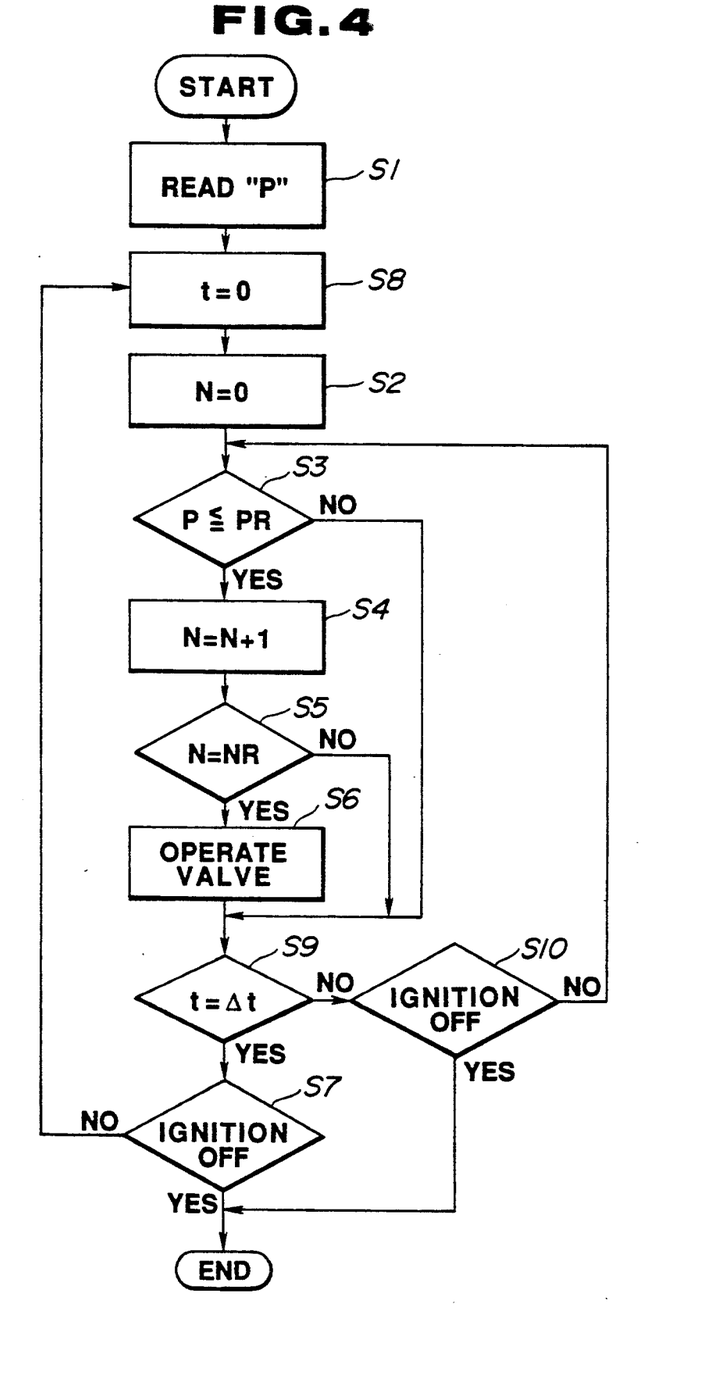
FIG. 4 is a flowchart which depicts the operation steps to be carried out by a micro-computer employed in a second embodiment of the present invention.

Referring to FIG. 4, there is shown a flowchart which depicts operation steps to be carried out in a second embodiment of the present invention.

Figure 6B:
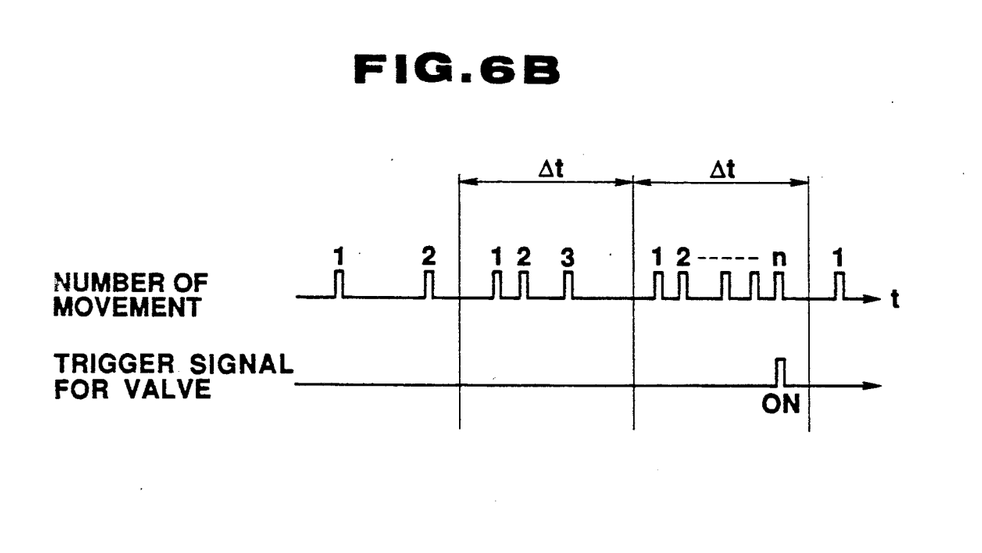

When a person (for example, a driver) sitting on the seat "S" turns an ignition switch ON, the program starts and at step S1, a pressure "P" applied to the pressure sensor 35 by the seat occupant is read. Then, at step S8, the timer 41 is reset, and at step S2, the counter 39 is reset. Then, at step S3, a judgement is carried out as to whether the pressure "P" is smaller than the reference value "PR" or not. If Yes, that is, when the pressure "P" is smaller than the reference value "PR", the counter counts "one" at step S4. If No, that is, when the pressure "P" is greater than the reference value "PR", the operation step goes to an after-mentioned step S9. At step S5, a judgement is carried out as to whether the number "N" counted by the counter 39 has reached to a predetermined number "NR" or not. If Yes, that is, when the number "N" has reached to the predetermined number "NR", a trigger signal is issued as is seen from FIG. 6B. Upon this, the computer 37 controls the valve 33 of the lumbar supporting air bag 19 to repeat ON-OFF operation for a given time thereby to force the lumbar supporting air-bag 19 to repeat the expansion-contraction operation (step S6). If at step S5, it is judged that the number "N" has not reached the predetermined number "NR", the operation step goes to step S9. At step S9, a judgement is carried out as to whether a predetermined time "Δt" has passed or not. If Yes, the operation step goes to step S7 wherein a judgement is carried out as to whether the ignition switch is OFF or not. If No at this step S7, the operation step goes back to step S8 to repeat the above-mentioned steps. If Yes at step S7, the control is stopped. If No at step S9, that is, when the predetermined time "Δt" has not passed yet, the operation step goes to step S10 wherein a judgement is carried out as to whether the ignition switch is OFF or not. If No, that is, when the engine is still operating, the operation step goes back to step S3 to repeat the above-mentioned steps. If Yes, the control is stopped.

Thus, in the second embodiment, when the number "N" which represents the number of the movement of the seat occupant exceeds the predetermined number "NR" within the predetermined time "Δt", the computer 37 controls the lumbar supporting air-bag 19 to repeat the expansion-contraction operation.

Figure 5:
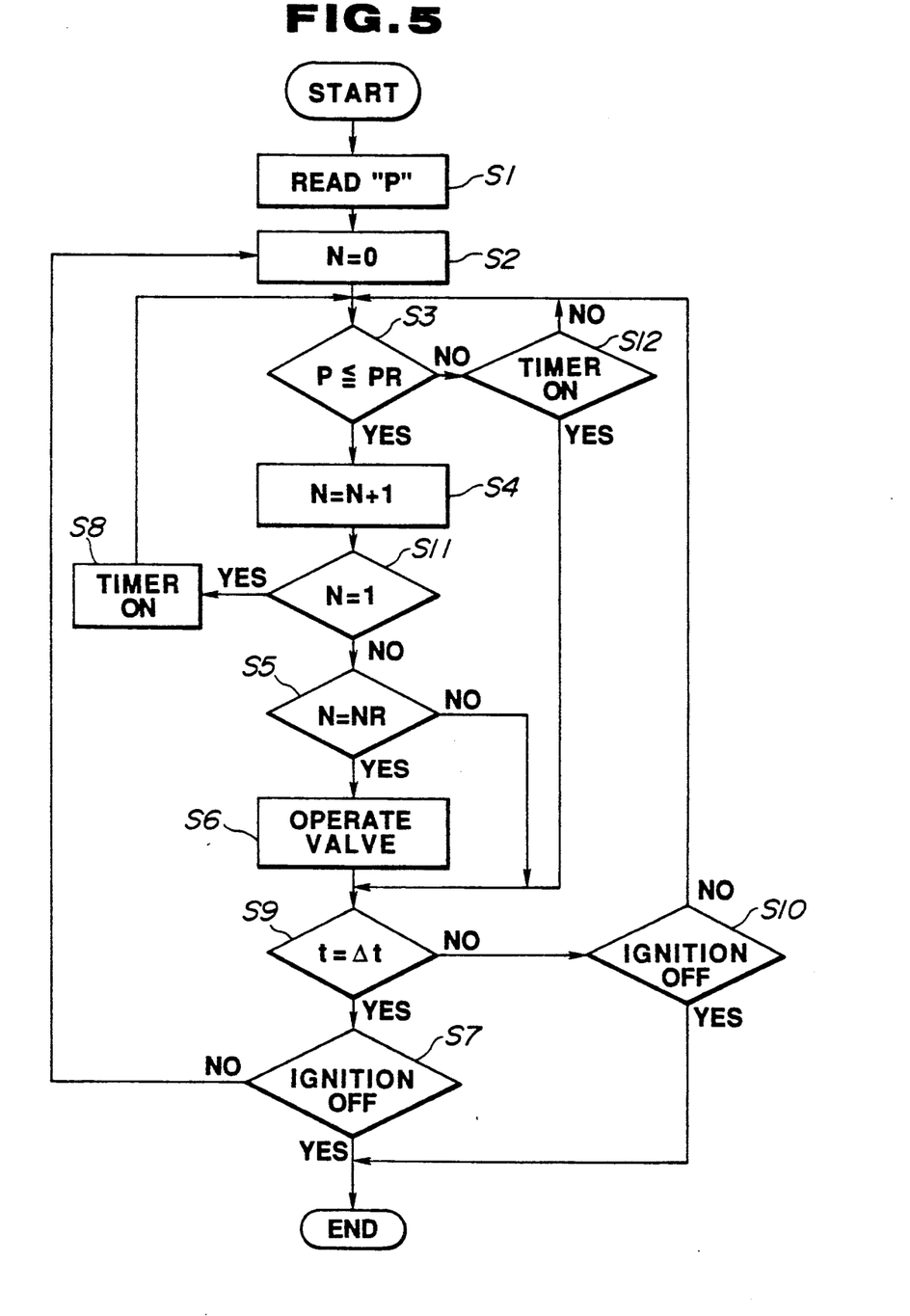
FIG. 5 is a flowchart which depects the operation steps to be carried out by a micro-computer employed in a third embodiment of the present invention.

Referring to FIG. 5, there is shown a flowchart which depicts operation steps to be carried out in a third embodiment of the present invention.

Figure 6C:
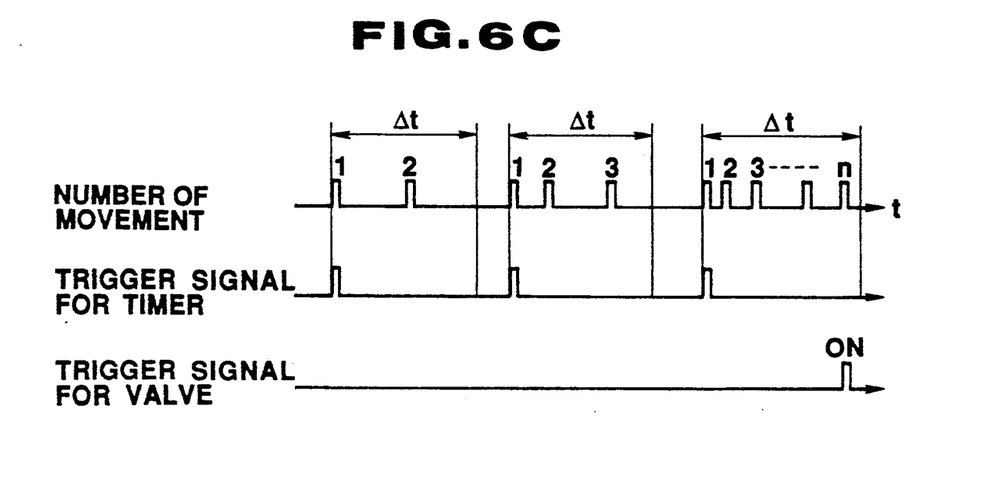

When a person (for example, a driver) sitting on the seat "S" turns an ignition switch ON, the program starts and at step S1, a pressure "P" applied to the pressure sensor 35 by the seat occupant is read. Then, at step S2, the counter 39 is reset. Then, at step S3, a judgement is carried out as to whether the pressure "P" is smaller than the reference value "PR" or not. If Yes, the counter 39 counts "one" at step S4. When, at step S11, the number "N" counted by the counter 39 is not one, the operation step goes to step S5 wherein a judgement is carried out as to whether the number "N" has reached to the predetermined number "NR" or not. If Yes at step S5, a trigger signal is issued as is seen from FIG. 6C. Upon this, the computer 37 controls the valve 33 of the lumbar supporting air-bag 19 to repeat ON-OFF operation for a given time thereby to force the lumbar supporting air-bag 19 to repeat the expansion-contraction operation (step S6). Then, the operation step goes to step S9 wherein a judgement is carried out as to whether a predetermined time "Δt" has passed or not. If Yes, the operation step goes to step S7 wherein a judgement is carried out as to whether the ignition switch is OFF or not. If No, that is, when the engine is still operating, the operation step goes back to step S2 to repeat the above-mentioned steps. If Yes at step S7, the control is stopped.

If, at step S3, it is judged No, that is, when the pressure "P" is greater than the reference value "PR", the operation step goes to step S12 wherein a judgement is carried out as to whether the timer 41 is ON or not. If Yes, the operation step goes to step S9. If No at step S12, the operation step goes back to step S3.

If, at step S11, the number "N" counted by the counter 39 is "one", the operation step goes to step S8 to make the timer 41 ON, and the operation step goes back to step S3.

If, at step S5, it is judged No, that is, when the number "N" has not reached to the predetermined number "NR", the operation step goes to step S9.

If, at step S9, it is judged that the predetermined time "Δt" has not passed yet, the operation step goes to step S10 wherein a judgement is carried out as to whether the ignition switch is OFF or not. If Yes, the control is stopped. While, if No, that is, when the engine is still operating, the operation step goes back to step S3.

Thus, in the third embodiment, the operation of the timer 41 starts only when the seat occupant feels somewhat fatigued. Thus, the fatigue detecting accuracy in the third embodiment is much improved as compared with the afore-described first and second embodiments.

In the following, modifications of the present invention will be described.

The pressure sensor 35 may be located at an upper portion of the seatback 5 or at the seat cushion 3.

In place of the lumbar supporting air-bag 19, other air-bags, such as, the hip supporting air-bag 15, the thigh supporting air-bag 17 and the side supporting airbags 21, 23, 25 and 27 may be used as the abovementioned massaging means.

An acceleration sensor may be employed for improving the fatigue detecting accuracy. That is, when an acceleration of the associated motor vehicle exceeds a predetermined degree, the movement of the seat occupant is so treated as not induce the counting of the counter 39 on the supposition that the movement has been caused by the acceleration. Furthermore, a shift operation sensor and a steered angle sensor may be employed for the improvement of the fatigue detecting accuracy. That is, when the sensors sense the shift operation and the steering operation which is beyond a given degree, the movement of the seat occupant is so treated as not induce the counting of the counter 39.

Another timer may be employed, which is arranged to start the operation of the counter 39 after a given time from the "ON" turning of the ignition switch. This is based on the supposition that just after engine starting, the seat occupant (viz., driver) tends to move frequently for obtaining a best sitting position.

As factors for detecting the degree of fatigue, Flicker value, Oculogyration, Electromyogram, Blood pressure and Skin temperature of the seat occupant can be used.

Flicker value: Barometer of indicating the consciousness level of cerebrum. When fatigued, the value is lowered.

Oculogyration (EOG): When driving lasts several hours, the amplitude and the frequency of EOG are both reduced and the blinking is increased.

Electromyogram (EMG): When a fatigue is felt, waveforms having large amplitude appear and the number of small waveforms is increased.

Blood pressure, Kemokinesis: When a portion, such as the hip portion of a seat occupant, is kept pressed for a long time, kemokinesis trouble tends to occur causing the fatigue.

Skin temperature: Skin temperature drop is sometimes caused by the kemokinesis trouble.

What is claimed is:

1. A seat control system comprising:
a seat with an occupant holding portion;
shape changing means located in said seat for changing the shape of said occupant holding portion;
detecting means located in said seat for detecting and counting a movement made by an occupant of said seat relative to said seat; and
control means connected to said detecting means and said shape changing means for controlling said shape changing means in accordance with a predetermined number of movements detected by said detecting means.

2. A seat control system comprising:
a seat with an occupant holding portion;
first means located in said seat for changing the shape of said occupant holding portion;
second means connected to said first means for controlling said first means at given intervals;
third means located in said seat for issuing an information signal representative of a movement and the number of movements made by an occupant of said seat relative to said seat; and
fourth means connected to said first, second, and third means for determining said given intervals in accordance with an information signal provided by said third means, which represents a predetermined number of movements made by said occupant to control said second means to change the shape of said first means.

3. A seat control system as claimed in claim 2, in which said first means comprises:
an air-pump;
a plurality of air-bags installed in given portions of the seat;
a plurality of pipes connecting the respective airbags to an outlet of said air-pump; and
electromagnetic valves mounted to the respective pipes to selectively open and close the same.

4. A seat control system as claimed in claim 3, in which said second and fourth means are incorporated with a computer.

5. A seat control system comprising:
a seat with an occupant holding portion;
shape changing means located in said seat for changing the shape of said occupant holding portion;
detecting means located in said seat for detecting and counting a movement made by an occupant of said seat relative to said seat; and
control means connected to said detecting means and said shape changing means for controlling said shape changing means in accordance with a predetermined number of movements detected by said detecting means,
wherein the count is reset to zero after said predetermined number of movements has been detected or after a predetermined interval.

6. A seat control system comprising:
a seat with an occupant holding portion;
first means located in said seat for changing the shape said occupant holding portion;
second means connected to said first means for controlling said first means at given intervals;
third means located in said seat for issuing an information signal representative of a movement and the number of movements made by an occupant of said seat relative to said seat; and
fourth means connected to said first, second, and third means for determining said given intervals in accordance with an information signal provided by said third means, which represents a predetermined number of movements made by said occupant to control said second means to change the shape of said first means,
wherein said third means is reset so that the information signal represents zero movement after said predetermined number of movements has reached or after a predetermined interval.

7. A seat control system comprising:
a seat with an occupant holding portion;
first means located in said seat for changing the shape of said occupant holding portion, said first means including an air-pump, a plurality of air-bags installed in given portions of said seat, a plurality of pipes connecting the respective air-bags to an outlet of said air-pump, and electromagnetic valves mounted to the respective pipes to selectively open an close the same;
second means connected to said first means for controlling said electromagnetic valves at given intervals;
third means located in said seat for issuing an information signal representative of a movement and the number of movements made by an occupant of said seat relative to said seat, said third means including a pressure sensor which is installed on a seatback portion of said seat at the position where the lumbar part of the occupant is to be placed, said pressure sensor detecting whether the occupant has moved by comparing the pressure detected with a predetermined comparison pressure; and
fourth means connected to said first, second, and third means for determining said given intervals in accordance with the information signal provided by said pressure sensor, which represents a predetermined number of movements made by said occupant to control said second means to change the shape of said first means,
wherein said second and fourth means are incorporated with a computer.

8. A seat control system as claimed in claim 7, in which one of said air-bag is positioned at said given part of the occupant holding portion of the seat, said given part being said position where the lumbar part of the occupant is to be placed.

9. A seat control system as claimed in claim 8, in which said third means includes counting means which counts the number of movements made by the seat occupant.

10. A seat control system as claimed in claim 9, in which said counting means calculates the number of movements made by the seat occupant from the information signal given by said pressure sensor.

11. A seat control system as claimed in claim 10, in which when the number of movements of the seat occupant reaches said predetermined number, said computer controls one of said electromagnetic valves to repeat ON-OFF operation for a given time, said one valve being associated with the air-bag positioned at said given part.

12. A seat control system as claimed in claim 11, in which said fourth means comprises a timer which determines the time within which the number of movements of the occupant calculated by said counting means reaches said predetermined number.

13. A seat control system as claimed in claim 12, in which said fourth means further includes another timer which functions to permit the substantial movement counting operation of said counting means after a given time from the start of said counting means.

* * * * *